United States Patent [19] [11] 3,975,425
Wassen [45] Aug. 17, 1976

[54] PROCESS FOR CARRYING OUT NITROSATION REACTIONS AND DIAZOTATION REACTIONS
[75] Inventor: Willem J. Wassen, Geleen, Netherlands
[73] Assignee: Stamicarbon B.V., Geleen, Netherlands
[22] Filed: Oct. 10, 1973
[21] Appl. No.: 405,078

[30] Foreign Application Priority Data
Oct. 14, 1972  Netherlands.................. 7213944

[52] U.S. Cl............................ 260/466; 260/149; 260/577; 260/579; 260/583 CC; 260/621 R; 260/647
[51] Int. Cl.² .................. C07C 77/00; C07C 76/00
[58] Field of Search .......... 260/466, 647, 577, 149, 260/579, 583 CC, 621 R

[56] References Cited
FOREIGN PATENTS OR APPLICATIONS
1,077,225   3/1960   Germany .......................... 260/647
509,204    7/1939   United Kingdom................ 260/466

Primary Examiner—Leland A. Sebastian
Attorney, Agent, or Firm—Cushman, Darby & Cushman

[57] ABSTRACT
Process for carrying out nitrosation reactions and diazotization reactions by reacting the concerning compound with a nitrite in the presence of an acid wherein ammonium-nitrite is used as the nitrite.

15 Claims, No Drawings

PROCESS FOR CARRYING OUT NITROSATION REACTIONS AND DIAZOTATION REACTIONS

The invention relates to a process to carry out nitrosation reactions and diazotization reactions.

As is known, nitrosation is understood to be a reaction in which the nitroso group (—N=O) is coupled to an N, a C or an O atom of an organic compound [see A. Turney and G. A. Wright, Chem. Revs. 59, 497–513 (1959)] by means of an nitrosating agent, usually nitrous acid.

As an example of a N-nitrosating reaction the nitrosation of a secondary aliphatic or aromatic amine may be mentioned, in which the N—N=O group is formed according to the equation:

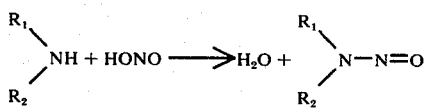
(I)

in which equation the letters $R_1$ and $R_2$ indicate alkyl- and/or aryl-groups in which $R_1$ and $R_2$ each represents an alkyl group having from 1–6 carbon atoms or an aryl group having from 6–14 carbon atoms and in which $R_1$ and $R_2$ together with the nitrogen atoms may form a ring structure having from 3—6 carbon atoms in the ring.

An example of a diazotization reaction is the reaction of nitrous acid with a primary aromatic amine, which diazotization proceeds via a nitrosation according to the equations:

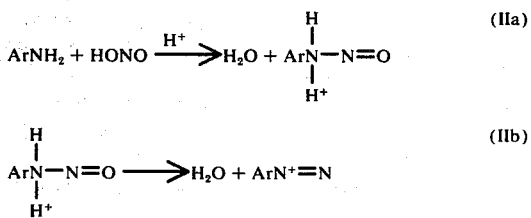

in which equations the letters Ar indicate an aryl group having from 6 to 14 carbon atoms As is known, primary aliphatic amines, unlike primary aromatic amines, do not yield a diazonium compound since the nitroso compound formed as an intermediate product decomposes directly, with formation of an alcohol and nitrogen.

The nitrosation of phenol, according to the equation

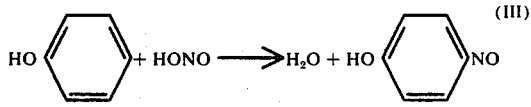
(III)

is an example of the coupling of the nitroso group to a carbon atom, whilst the formation of nitrite esters of aliphatic alcohols, according to equation:

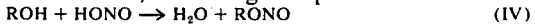
ROH + HONO → H$_2$O + RONO    (IV)

in which the letter R indicates an alkyl group with 1—10 carbon atoms or a cycloalkyl-group with 6–10 carbon atoms, represents the coupling of the nitroso group to an oxygen atom.

The nitrous acid applied as the nitrosating agent in these reactions is not durable and, for this reason in reactions of this kind an alkali nitrite or an earth-alkali nitrite is invariably used as a raw material, from which, during the nitrosation reaction, nitrous acid is liberated in situ by means of an inorganic acid, usually hydrochloric acid or sulphuric acid.

Under certain circumstances, viz. those in which ammonia and nitrous gases are avialable, it would be an attractive idea, if it should be possible, in the case of nitrosation reactions to start from ammonium nitrite instead of from alkali nitrite or earth-alkali nitrite as a raw material for the production of nitrous acid in situ.

For, in that case an ammonium nitrite the scanning and selection can be prepared in a cheap manner from the products already present, by absorption of nitrous gases in ammonia.

So far said idea has not been put into effect because of the knowledge of the decomposition of ammonium nitrite into nitrogen and water, which decomposition proceeds particularly rapidly especially in an acid medium, owing to which ammonium nitrite seems not suitable for use as a raw material for the formation of nitrous acid.

It has now been found however that the spontaneous decomposition of ammonium nitrite in an acid medium does not, or practically not, take place in the presence of a reactant into which a nitroso group can be introduced; as a result of this, an ammonium nitrite solution or solid ammonium nitrite can very well be used as a starting material for nitrosating reactions. Efficiencies are thereby achieved of the same order of magnitude as those one would be obtained with application of alkali nitrite or earth-alkali nitrite, other conditions being the same. The temperature at which the reaction is carried out may range from about −10° to 30°C, preferably temperatures of 0° to 15°C are used.

In order to elucidate the invention, the following examples are given.

No., I

Preparation is p-nitrosophenol

For the preparation of p-nitrosophenol, 0.319 mole of phenol, 0.393 mole of ammonium nitrite in the form of a 29.2% by weight solution in water, 0.755 mole of sodium hydroxide and water made up to a total of 38.4 moles were combined in a stirred and cooled round-bottom flask. The sodium hydroxide was added to cause the phenol to dissolve. The resulting solution was cooled to 2°C, whereupon, in 1 hour, a total of 0.765 mole of H$_2$SO$_4$ dissolved in 11.15 moles of H$_2$O was gradually added, the temperature of the reaction mixture being kept below 5°C.

After the addition of sulphuric acid had been stopped, the reaction mixture was filtered and the resulting mass of p-nitrosophenol washed with ice water. The yield of p-nitrosophenol, which had a purity of more than 98%, amounted to 69% referred to the phenol.

EXAMPLE II

Preparation of methyl nitrite ester

For the preparation of methyl nitrite ester, 0.626 mole of methanol and 0.220 mole of ammonium nitrite in the form of a 21.6% by weight solution in water were combined in a stirred reactor. The solution was cooled to 12°C, whereupon, in 1 hour, a total of 0.250 mole of $H_2SO_4$, diluted with 2.51 moles of $H_2O$, was slowly added to the reaction mixture.

The temperature of the reaction mixture was kept to 12°C by cooling.

The liberated gaseous methyl nitrite was caught in a cold stage of dry ice, condensed and redistilled. The yield of methyl nitrite amounted to 85% referred to the methanol quantity.

EXAMPLE III

Diazotization of aniline 0.250 mole of aniline, 0.635 mole of hydrochloric acid (as a 36% by weight aqueous solution) and a total of 4.3 moles of water were added to a stirred round-bottom flask.

The solution obtained was given a temperature of 0°C by cooling, whereupon, with stirring and in 1 hour's time, 0.275 mole of ammonium nitrite in the form of a 21.3% by weight aqueous solution was gradually added. The reaction temperature was kept to 0°C.

The resulting acid solution of benzene diazonium chloride

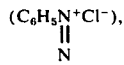

to the scanning and selection which had a temperature of 0°C, was added dropwise in half an hour, with stirring, to the coupling agent, floroglucinol $[C_6H_3(OH)_3]$ (0.250 mole dissolved in 225 cm³ of methanol and 25 cm³ of water).

The temperature of the reaction mixture was kept at 25°C. Next, the reaction mixture was cooled to 0°C and filtered, following which the solid red reaction product was washed with a mixture of methanol and water and then dried in a vacuum drying oven at 50°C.

The yield of the product, trihydroxyazobenzene $[C_6H_5N=NC_6H_2(OH)_3]$ amounted to 92% referred to the aniline originally present.

For implementation on a commercial scale, the nitrosation reactions and the diazotization reactions may be carried out with ammonium nitrite solutions, as are processed in the preparation of hydroxyl ammonium sulphate according to the Raschig process; the solutions of ammonium nitrite, which contain 1–6% by weight of $NH_4NO_3$ by the side of 20–35% by weight of $NH_4NO_2$ and which are then obtained by absorption of nitrous gases in ammonia-water which may or may not contain carbonate, can without further measures be used as a raw material for the formation of nitrous acid in the described processes for nitrosation and for diazotization.

What is claimed is:

1. Process to carry out nitrosation reactions and diazotization reactions, in which a compound which is (1) phenol, (2) an aliphatic alcohol, (3) a primary aromatic amine of the formula $ArNH_2$ wherein Ar is an aryl of 6 to 14 carbon atoms or (4) a secondary amine of the formula $R_1-NH-R_2$ wherein each of $R_1$ and $R_2$ is alkyl of from 1 to 6 carbon atoms or aryl of from 6 to 14 carbon atoms into which a nitroso group can be introduced is reacted with a nitrite in the presence of an acid, this process being characterized in that ammonium nitrite is applied as the nitrite.

2. Process according to claim 1, characterized in that said ammonium nitrite is used in the form of a 20–35% by weight aqueous solution obtained by absorption of nitrous gases in ammonia water or in a solution containing ammonium carbonate.

3. The process of claim 1, wherein said compound is reacted with ammonium nitrite at temperatures between −10° to 30°C.

4. The process of claim 3, wherein said temperature is between 0° and 15°C.

5. In a process for coupling a nitroso group to a carbon atom of phenol by reacting said phenol with a nitrite in the presence of an acid, the improvement comprising using ammonium nitrite as said nitrite.

6. The process of claim 5, wherein said ammonium nitrite is used in the form of a 20–35% by weight aqueous solution obtained by absorption of nitrous gases in ammonia water or in a solution containing ammonium carbonate.

7. The process of claim 5, wherein said compound is reacted with ammonium nitrite at a temperature between −10° to 30°C.

8. In a process for coupling a nitroso group to an oxygen atom of an aliphatic alcohol by reacting said alcohol with a nitrite in the presence of an acid, the improvement comprising using ammonium nitrite as the source of said nitrite.

9. The process of claim 8, electrophotographic said ammonium nitrite is used in the form of a 20 to 35% by weight aqueous solution obtained by absorption of nitrous gas in ammonia water or in a solution containing ammonium carbonate.

10. The process of claim 8, wherein said compound is reacted with ammonium nitrite at temperatures between −10° to 30°C.

11. The process of claim 8, wherein said compound is methanol.

12. In a process for coupling a nitroso group to a nitrogen atom of a primary or secondary amine wherein said primary amine is a primary aromatic amine of the formula $ArNH_2$ wherein Ar is an aryl of 6 to 14 carbon atoms and wherein said secondary amine is of the formula $R_1-NH-R_2$ wherein each of $R_1$ and $R_2$ is alkyl of from 1 to 6 carbon atoms or aryl of from 6 to 14 carbon atoms by reacting said amine with a nitrite in the presence of an acid, the improvement comprising using ammonium nitrite as the source of said nitrite.

13. The process of claim 12, wherein said ammonium nitrite is used in the form of a 20 to 35% by weight aqueous solution obtained by absorption of nitrous gases in ammonia water or in a solution containing ammonium carbonate.

14. The process of claim 12, wherein said compound is reacted with ammonium nitrite at temperatures between −10° to 30°C.

15. The process of claim 12, wherein said compound is an aromatic amine.

* * * * *